United States Patent [19]

Fountain et al.

[11] Patent Number: 4,610,868
[45] Date of Patent: Sep. 9, 1986

[54] LIPID MATRIX CARRIERS FOR USE IN DRUG DELIVERY SYSTEMS

[75] Inventors: Michael W. Fountain, Plainsboro; Steven J. Weiss, Lawrenceville; John J. Kearns, Princeton; Alan L. Weiner; Mircea C. Popescu, both of Plainsboro, all of N.J.

[73] Assignee: The Liposome Company, Inc., Princeton, N.J.

[21] Appl. No.: 591,576

[22] Filed: Mar. 20, 1984

[51] Int. Cl.$^4$ .................. A61K 43/00; A61K 49/00
[52] U.S. Cl. ............................. 424/1.1; 264/4.1; 264/4.32; 424/9; 424/22; 424/31; 428/402.2; 435/1
[58] Field of Search ............... 424/1.1, 9, 22, 31; 428/402.2; 264/4.1, 4.32; 435/1

[56] References Cited

U.S. PATENT DOCUMENTS

| | | | |
|---|---|---|---|
| 3,159,545 | 12/1964 | Kidwell et al. | 424/1.1 |
| 3,159,600 | 4/1965 | Brockett | 428/402.2 |
| 3,993,754 | 11/1976 | Rahman et al. | 424/177 |
| 4,010,038 | 3/1977 | Iwaski et al. | 264/4.3 |
| 4,145,410 | 3/1979 | Sears | 424/19 |
| 4,224,179 | 9/1980 | Schneider | 424/36 |
| 4,235,871 | 11/1980 | Papahadjopoulos et al. | 424/19 |
| 4,298,594 | 11/1981 | Sears | 424/19 |
| 4,310,506 | 1/1982 | Baldeschwieler et al. | 424/1.1 |
| 4,317,743 | 3/1982 | Chang | 424/32 |
| 4,349,529 | 9/1982 | Morcos et al. | 128/659 |
| 4,356,167 | 10/1982 | Kelly | 424/38 |
| 4,377,567 | 3/1983 | Geho | 424/1.1 |
| 4,404,183 | 9/1983 | Kawata et al. | 424/22 |
| 4,434,153 | 2/1984 | Urquhart et al. | 424/22 |
| 4,460,560 | 7/1984 | Tökes et al. | 424/1.1 |

OTHER PUBLICATIONS

Bligh and Dyer, Can. J. Biochem. Physiol., 37:911, (1959).
Gregordiadis, G. et al., eds. in Targeting of Drugs, 268–272, Plenum Press, New York, 1982.
Gregordiadis, New England Med., 295: 704, (1976).
Ostro et al., in Liposomes and Immunobiology, Elsevier North Holland, Inc., eds. B. Tom and H. Six, 225–239, (1980).
Schroeder, Proceedings of the Controlled Release Society Meeting, San Francisco, Jul. 1983.

*Primary Examiner*—Christine M. Nucker
*Attorney, Agent, or Firm*—Pennie & Edmonds

[57] ABSTRACT

Lipid matrix carriers are described which provide for the sustained release of bioactive agents *in vivo* or *in vitro*. The properties of the lipid matrix carriers of the present invention include high entrapment efficiencies; release of entrapped compounds in their active form; biodegradability and avoidance of vascular occlusion *in vivo;* and avoidance of sequestration of the bioactive agent in the liver and spleen.

105 Claims, 6 Drawing Figures

FIG. 1

Retention of Gentamicin in the Area of Inoculation
After Intramuscular Injection

FIG. 2

Recovery of Gentamicin From Urine of Mice After Intramuscular Injection

FIG. 3

Recovery of Oxytetracycline From Urine of Mice After Intramuscular Injection

FIG. 4

Recovery of Oxytetracycline From Urine of Mice After Subcutaneous Injections

FIG. 5

Saability of LMCs in Serum

FIG. 6

Treatment of Joint Arthritis

LIPID MATRIX CARRIERS FOR USE IN DRUG DELIVERY SYSTEMS

TABLE OF CONTENTS

Field of the Invention
Background of the Invention
    Carrier Systems
Summary of the Invention
Brief Description of the Figures
Detailed Description of the Invention
    Preparation of LMCs
    Characterization of LMCs
        Physical Structure
        Physical Size Determination
        Composition
        Degree of Entrapment
    Physiological Responses to LMCs
Example: Preparation of LMCs
    Incorporation of Water Soluble Materials
        Streptomycin
        Gentamicin
        Oxytetracycline
    Incorporation of Lipid Soluble Materials
        Indomethacin
        Diazepam
    Effect of Drug Concentration and Method of Preparation upon LMC Loading
        Gentamicin
        Oxytetracycline
Example: Uses of LMCs
    Sustained Release of Gentamicin from LMCs after Intramuscular Injection in Mice
    Sustained Release of Oxytetracycline from LMCs after Intramuscular Injection in Mice
    Sustained Release of Oxytetracycline from LMCs after Subcutaneous Injection in Mice
Example: Stability of LMCs
    LMCs in Serum
    LMCs in Vivo
Example: Treatment of Joint Arthritis
Example: Topical Administration of LMCs for Localized Delivery

FIELD OF THE INVENTION

This invention relates to novel lipid complexes and to their use as carriers in delivery systems. More specifically, stable carriers composed solely or primarily of lipids are described which provide for the sustained and controlled release of drugs or other biological materials. This is most clearly illustrated following intramuscular injection, although other routes may be utilized.

The compositions and methods described herein offer substantial advantages over traditional liposomes and other delivery systems. The practice of the present invention is demonstrated by the entrapment of streptomycin, gentamicin, indomethacin or diazepam in the carriers of the present invention and by its application to the controlled release in vivo of gentamicin, oxytetracycline, and indomethacin.

BACKGROUND OF THE INVENTION

CARRIER SYSTEMS

Liposomes are closed bilayer membranes containing an entrapped aqueous volume. Liposomes may be any variety of unilamellar vesicles (possessing a single membrane bilayer) or multilamellar vesicles (onion-like structures characterized by concentric lipid bilayers, each separated from the next by an aqueous layer).

Much has been written regarding the potential use of liposomes as drug delivery systems. In a liposomal drug delivery system, the medicament is entrapped during liposome formation and then administered to the patient to be treated. Typical of such disclosure are U.S. Pat. Nos. 3,993,754 issued on Nov. 23, 1976 to Rahman and Cerny, 4,145,410 issued on Mar. 20, 1979 to Sears, 4,235,871 issued Nov. 25, 1980 to Paphadjopoulos and Szoka, 4,224,179 issued Sept. 23, 1980 to Schneider, 4,356,167 issued Oct. 26, 1982 to L. Kelly, and 4,377,567 issued Sept. 13, 1979 to Geho.

Some of the problems encountered in using liposome preparations include instability of the liposomes during storage (e.g., liposomes cannot be stored as a dry powder); low entrapment of the incorporated drug; and the inability to completely decay in vivo so that a residual dose of the drug remains in the system (i.e., incomplete clearance of the drug).

A number of non-liposomal drug delivery systems have been described. In one, Schroder [Proceedings of the Controlled Release Society Meeting, San Francisco, July, 1983] used an aqueous carbohydrate solution in conjunction with an emulsifying system which, through sonication, effectively entrapped a number of proteins. When this preparation was added to acetone, spherical microcarriers of exceptional stability precipitated. Unfortunately, the stability of Schroder's microcarriers was such that the half-time for release of a number of proteins ranged from 5 to 15 days. When applied in vivo, such extreme carrier stability and resistance to biodegradation could lead to an immune reaction against the carrier, granuloma formation and/or capillary occlusion. (Targeting of Drugs, G. Gregoriadis, J. Senior and A. Trouet, eds., 268–272, Plenum Press, New York, 1982).

Chang (U.S. Pat. No. 4,317,743 issued Mar. 2, 1982) developed a microcapsule carrier composed of polyisocyanatoamide that entrapped hydrophobic substances, such as chemical dyes. These carriers displayed high heat stability and humidity resistance. At the same time, however, their formation required temperatures that would preclude their use as carriers of many pharmaceutical agents which are denatured at these temperatures. Moreover, their extreme stability necessitated the application of pressure, high temperature or other physical disruptive methods to cause the release of entrapped compounds.

Another type of delivery vehicle was developed by Sears (U.S. Pat. No. 4,298,594 issued Nov. 3, 1981). Using two synthetic approaches, Sears produced xenobiotic delivery vehicles composed of phospholipids and phospholipid-immiscible constituents, such as cholesterol esters or triglycerides. The result was microcarriers having diameters of 130–1000 angstroms and phospholipid compositions claimed to range from about 50 to 97 mole percent. However, these values appear to pertain to starting ratios, and no data are given as to how, or whether, the actual product composition was measured. These microcarriers were extremely stable at 37° C. in buffered saline solution, showing no change in particle size after 30 days of incubation.

SUMMARY OF THE INVENTION

The present invention presents new and significantly improved methods for the preparation of a new type of carrier structure composed of lipids and compounds such as biologically active agents which, when administered in vivo or in vitro, provides for the sustained release of the incorporated material, and which, hereinafter will be referred to as lipid matrix carriers (LMCs).

These carriers are both structurally and behaviorally different from other carrier structures such as liposomes, microspheres, microcapsules, microreservoirs, or carbohydrate crystal matrices. As a result of these differences, LMCs overcome many of the problems presented by previous carrier systems.

Advantages of the LMCs of the present invention include: (1) the ability to incorporate both water-soluble and lipid-soluble compounds in the carrier matrix; (2) a high level of entrapment of the incorporated compound in the carrier matrix (e.g., depending upon the method of preparation, 100% of the added compound can be incorporated in the LMCs); (3) the ability to control drug leakage by varying the size of the LMCs and the composition of the lipids used in LMC formation, which, in turn, is a function of the methodology used to prepare the LMCs; (4) stability in dry storage; and (5) the ease of preparation of pure populations of LMCs.

LMCs are globular structures composed of a hydrophobic compound and an amphipathic compound. The diameter of the LMCs ranges from about 500 nm to about 100,000 nm. The final composition of the LMC structures may be determined by separating the hydrophobic and amphipathic components by high pressure liquid chromatography and assaying the separated components spectrophotometrically by measuring absorbance at a wavelength of 205 nm. By this analysis the final concentration of the amphipathic component of LMCs ranges from about 2% to about 35%, by weight, of the water insoluble components of the LMCs. If a surfactant is added during the preparation of LMCs the final concentration of the amphipathic component can range from about 2% to about 50% of the water insoluble components of the LMCs.

The properties of LMCs include: (1) high encapsulation efficiencies for the entrapment of materials; (2) the release of entrapped compounds in bioactive form; (3) biodegradability in vivo; (4) avoidance of vascular occlusion; and (5) a large size that prevents carrier circulation from an intramuscular depot.

BRIEF DESCRIPTION OF THE FIGURES

To more fully comprehend the invention, reference should be made to the accompanying figures, in which.

DETAILED DESCRIPTION OF THE INVENTION

PREPARATION OF LMCs

LMCs are lipid complexes with properties not shared by previously described lipid carrier vehicles. Their preparation may be carried out using one of two basic approaches, depending upon the solubility properties of the material that is to be entrapped. In either case, a wide range of lipid materials may be employed.

Two general classes of lipids comprise the LMCs of the present invention. Present in greatest abundance are highly hydrophobic compounds, the requirement for which in the preferred embodiment is satisfied by triglycerides. Corn oil serves as a convenient and economical source of mixed triglycerides, but other vegetable oils, including but not limited to palm kernel oil, coconut oil, soybean oil, sunflower oil, safflower oil, cocoa butter, and the like may be used. Specific molecular species might be employed as well. Such species may include, but are not limited to, trilaurin, trimyristin, tripalmitin and tristearin, or other glyceryl esters in which the fatty acyl chains of these compounds as well as other fatty acids are incorporated in a non-homogeneous fashion. Other broad classes of long chain hydrophobic compounds such as the wide range of cholesterol esters may be used. It has even been found that long chain organic mixtures such as petroleum jelly are acceptable.

Cholesterols, and other sterols, α-tocopherol and other lipid-soluble vitamins may also be employed as LMC structural components, although they are normally viewed as materials to be entrapped. The only constraint appears to be that the hydrophobic compounds selected should, when uncomplexed with the other components of this invention, be soluble in the organic solvent chosen.

The second broad class of lipid materials used in the preparation of LMCs of this invention are amphipathic in character. Hydrophilic character could be imparted to the molecule through the presence of phosphato, carboxylic, sulphato, amino, sulfhydryl, nitro, and other like groups. Hydrophobicity could be conferred by the inclusion of groups that include, but are not limited to, long chain saturated and unsaturated aliphatic hydrocarbon groups and such groups substituted by one or more aromatic, cycloaliphatic or heterocyclic groups. The preferred amphipathic compounds are phosphoglycerides, representative examples of which include phosphatidylcholine, phosphatidylethanolamine, lysophosphatidylcholine, lysophosphatidylethanolamine, phosphatidylserine, phosphatidylinositol, phosphatidic acid and diphosphatidylglycerol. Synthetic saturated compounds such as dimyristoylphosphatidylcholine, dipalmitoylphosphatidylcholine or distearoylphosphatidylcholine or unsaturated species such as dioleoylphosphatidylcholine or dilinoleoylphosphatidylcholine might also be usable. In the preferred embodiment, egg phosphatidylcholine is used. Other compounds lacking phosphorous such as members of the sphingolipid and glycosphingolipid families might also be used. These compounds may be obtained from natural sources or they may be synthetic.

Where water soluble materials are to be entrapped, the preferred approach is to combine with a relatively small volume of water, saline solution, or buffered medium, the hydrophobic and amphipathic lipid components and the water soluble pharmaceutical or other material to be entrapped, and to simultaneously or subsequently apply energy to the system. The volume of the aqueous phase typically ranges from about 0.7% to about 10.25% of the volume of the lipid components used. The application of energy is most conveniently and controllably made by sonication, but vigorous magnetic or mechanical stirring, vortexing, linear or gyrorotary shaking or other means of agitation could also be used. Because the lipid components are in relative abundance, the result is a water-in-oil emulsion, the aqueous portions of which contain the material to be entrapped. Where thermally sensitive compounds such as oxytetracycline are to be entrapped and probe sonication is used, the temperature of the mixture should be kept below about 4° C. Otherwise, the compound will precipitate and break down the emulsion.

The emulsion formed is then extruded through an appropriate orifice into an organic solvent, with agitation or stirring. Extrusion through a syringe with a needle of defined gauge is most convenient, although many alternative means would suffice. The organic solvent of choice could be acetone, ethanol, diethyl ether, petroleum ether, or one of a number of similar solvents. The choice of an appropriate organic solvent will depend upon the solubility characteristics of the lipids used during LMC formation. Ethanol would be superior because of its lower toxicity, where use of the LMCs of the present invention is contemplated for subcutaneous or intramuscular injection, or for a number of other routes of administration. The essential requirements for such solvent are the ability to extract the lipid components that do not become incorporated into the LMC complex and to remove free or non-entrapped water from the LMCs produced. The introduction of the emulsion into the organic solvent immediately gives rise to LMCs, which are then isolated in a manner described infra. The temperature chosen for these operations may vary from about 4° C. to about 70° C., depending upon the factors of convenience and the thermal stability of the material to be incorporated.

Variations of this method may readily be envisioned by those skilled in the art. For example, the hydrophobic and amphipathic lipid components may be solubilized in the organic solvent to which the aqueous phase containing the bioactive agent is added. In that case, no water-in-oil emulsion would be formed and it is desirable to saturate the organic solvent with the lipid soluble components. In fact, prior saturation of the organic solvent with the lipid soluble components might be desirable even if they are also emulsified with the aqueous phase. Control of the final concentrations of the lipid components would be simplified, because extensive extraction by the organic solvent would not be possible. Where the organic solvent is not first saturated with the hydrophobic and amphipathic components, some of the lipids will enter the solvent and be unavailable for incorporation into LMCs. The final ratio of amphipathic to hydrophobic components may thus be modified by prior saturation of the organic solvents with the lipid soluble LMC components.

Alternatively, the aqueous phase may be eliminated entirely, and the material to be entrapped can be added to the lipid components directly. In this case, no water-in-oil emulsion is formed and the mixture is extruded into the organic solvent in order to form the LMCs. Entrapment of the material is greatly enhanced when water is eliminated; in fact according to this method, up to 100% of the added material can be entrapped in the LMCs.

A second basic method of LMC preparation is applicable to the entrapment of lipid soluble materials. In the preferred approach, the lipid soluble material to be entrapped is dissolved in the organic solvent to which the hydrophobic and amphipathic components are added. The resulting solution is then extruded into the aqueous component with agitation. The organic solvent may then be removed from the resulting suspension of LMCs. Again, the introduction of the lipid components may be varied from the aqueous to the organic phases as desired.

The rate of combination of the organic and aqueous components and the diameter of the extrusion orifice are critical determinants of LMC size. In general, extrusion through a small hypodermic syringe needle or pasteur pipette tip at a slow rate of flow will produce smaller LMC structures, and vice-versa. Rapid extrusion through a 16-gauge needle produces very large, unstable structures which coalesce into an oily mass. Best results have been obtained by slow extrusion through a 21-gauge needle, or its equivalent. Generally, the extrusion of a 10 ml volume through a 21-gauge needle should take about 5 minutes.

The above procedures may be further modified by the substitution of a chemical surfactant for the amphipathic lipid or by the addition of a surfactant to the amphipathic lipid. Such surfactants include but are not limited to members of the following chemical families: the N-acylsarcosinates, the polyethoxycarboxylates, the alkylbenzenesulfonates, the dialkyl sulfosuccinates, the sodium N-acyl-N-alkyltaurates, the alkyl sulfates, the long-chain phosphate esters, and the polyoxyethylene derivatives of sorbitan fatty acid esters (e.g. Tween 80). Surfactants used in complete substitution of the amphipathic lipid component lead to the production of relatively unstable LMCs. When used in low levels in combination with an amphipathic lipid, they may lead to enhanced product stability. Thus LMCs prepared with phosphatidyl choline and Tween 80 (polyoxyethylene sorbitan monooleate) together were more stable than those made with the phospholipid alone. The incorporation of surfactants may also be beneficial where the material to be entrapped is in some sense incompatible with the typical phospholipid or other amphipathic component.

Once LMCs are formed through the mixing of the aqueous and organic solvent components, they are separated from the unincorporated components. This could be accomplished easily by sedimentation or by some comparable means. Vestiges of the organic solvent may then be removed by any evaporative technique, such as by passing a stream of inert gas, by warming or by placing the LMCs under a vacuum. Once properly dried, LMCs stored in an atmosphere that prevents lipid oxidation (e.g. under nitrogen) are stable for many months. As needed, they may then be simply resuspended in water or any aqueous buffer before use.

CHARACTERIZATION OF LMCs

PHYSICAL STRUCTURE

LMCs are large globular structures which bear superficial resemblance to oil droplets. This appearance is misleading, however, since there is no tendency to coalesce as would occur with true oil droplets. Freeze fracture analysis reveals an absence of discrete internal organization, with no discernible bi-lamellar lipid structures. Because LMCs are generally hydrophilic, it is presumed that some of their amphipathic constituents are positioned with their hydrophilic heads exterior and their hydrophobic side chains in proximity to the interior of the matrix. The hydrophobic lipids, the remainder of the amphipathic components and the material entrapped are probably arranged in unstructured associations that are dictated by thermodynamic forces.

PHYSICAL SIZE DETERMINATION

The LMCs of the present invention have been examined by light microscopy, and their size has been approximated by comparison to calibrated latex beads. These examinations have shown that LMCs are far larger than the dimensions of other lipid microcarrier systems. Typically, LMCs measure about 500 nm to 100,000 nm in diameter. The production of such large lipid structures as has been noted above is dependent in part upon the conditions under which the aqueous and organic solvent components are combined.

More critical still is the ratio of the hydrophobic to the amphipathic component used in the preparation of LMCs; this ratio preferably ranges from about 1:1 to about 20:1, respectively, on a weight basis. Ratios smaller than unity tend to produce not LMCs but small, vesicular, liposomal structures. Ratios greater than about 20:1 produce an increasingly large fraction of huge structures that are intrinsicly unstable. Such large structures tend to collapse by coalescence into each other, with the formation of large oil droplets.

Within the preferred range, variations in the ratio of the hydrophobic to amphipathic lipid component used to prepare LMCs have little practical effect on the in vivo efficacy of LMCs. Higher proportions of the amphipathic component, however, tend to produce enhanced storage stability.

COMPOSITION

The lipid composition of the LMC product has been determined by separating the hydrophobic and amphipathic components by high pressure liquid chromatography and assaying the separated components spectrophotometrically by measuring absorbance at a wavelength of 205 nm. By this analysis, the final concentration of the amphipathic component of the LMCs ranges from about 2% to about 35%, by weight, of the water insoluble components of the LMCs. Where a surfactant is added to the amphipathic ingredient during the preparation of LMCs, the final concentration of the amphipathic component may be as high as 50%, by weight, of the water insoluble components of the LMCs.

To illustrate this, the composition of LMCs composed of egg phosphatidylcholine and corn oil with entrapped oxytetracycline was analyzed as described above. To this end, two LMC populations were prepared as follows:

(1) LMC-200: 8 ml corn oil, 100 mg egg phosphatidylcholine and 0.4 ml saline containing 200 mg oxytetracycline were mixed vortically to form a water-in-oil emulsion. The LMCs were formed by extruding the emulsion through a 21 gauge needle into 20 ml acetone which had previously been saturated with 100 mg egg phosphatidylcholine (i.e., the total amount of phosphatidylcholine used in the emulsion and in the acetone was 200 mg).

(2) LMC-110: these LMCs were prepared exactly as described for LMC-200 except that only 10 mg egg phosphatidylcholine was used to prepare the water-in-oil emulsion; as a result the total amount of phosphatidylcholine used in the emulsion and in the acetone was 110 mg.

Each of the LMC preparations was then pelleted by centrifugation at 6,500 x g for 10 minutes. A stream of nitrogen was passed over the pellets to dry the pellets and remove residual acetone.

The lipid components of each LMC pellet were extracted using a chloroform/hexane/water solvent system according to the method of Bligh and Dyer (1959, Can. J. Biochem. Physiol. 37:911); the lipids were removed from the chloroform phase by evaporating the chloroform to obtain a residue of the lipids. The lipid residue obtained from each LMC preparation was washed twice in hexane in order to remove all the residual chloroform which would interfere with the absorbance assay. The lipids were then dissolved in 8 ml hexane; samples of the hexane solution were diluted 1:4 with hexane and analyzed by separating the lipid constituents by high pressure liquid chromatography (HPLC) in a Beckman Gradient High Pressure Liquid Chromatograph Model 110A (Beckman Instruments, Inc., Fullerton, CA) as follows: for each sample a 20 $\mu$l aliquot was injected into a normal phase column ($\mu$Porasil, Waters Associates, Inc., Millford, MA). The mobile phase consisted of a gradient comprising hexane/isopropanol/water at a starting ratio of 6:8:0.75 and final ratio of 6:8:1.4, respectively.

Separation was detected spectrophotometrically by measuring absorbance of the outflow at a wavelength of 205 nm. Sharp peaks representing the triglycerides were detected after 1.85 minutes whereas the peaks representing phosphatidylcholine were detected after 21.1 minutes. (See Ostro, et. al., 1980, in Liposomes and Immunobiology, Elsevier North Holland, Inc., eds. B. Tom and H. Six, pages 225–239). The concentration of each component was computed from the area under each peak in the profile after a standard curve was generated for identically processed control samples containing known concentrations of egg phosphatidylcholine and triglycerides (corn oil).

The results of the HPLC separation and spectrophotometric analysis revealed that the LMC-200 product contained 200 mg egg phosphatidylcholine per 2700 mg triglycerides; that is, a final composition of approximately 7% phosphatidylcholine and 93% triglycerides by weight (or, assuming an average molecular weight of 750 for the triglycerides, approximately 6.6 mole % egg phosphatidylcholine and 93.4 mole % triglycerides). The LMC-110 product contained 52.8 mg egg phosphatidylcholine per 2600 mg triglycerides; that is, a final composition of approximately 2% egg phosphatidylcholine and 98% triglycerides by weight (or assuming an average molecular weight of 750 for the triglycerides, approximately 1.9 mole % egg phosphatidylcholine and 98.1 mole % triglycerides).

DEGREE OF ENTRAPMENT

Virtually any bioactive compound can be entrapped within a LMC. Such compounds include but are not limited to antibacterial compounds, antiviral agents, antifungal compounds, anti-parasitic compounds, tumoricidal compounds, anti-metabolites, peptides, proteins, toxins, enzymes, polypeptides, hormones, neurotransmitters, glycoproteins, lipoproteins, immunoglobulins, immunomodulators, vasodilators, dyes, radiolabels, radio-opaque compounds, fluorescent compounds, polysaccharides, plant lectins, anti-proteases, cell receptor binding molecules, anti-inflammatories, antiglaucomic agents, mydriatic compounds, local anesthetics, narcotics, vitamins, nucleic acids, polynucleotides, etc.

Two or more compounds may be simultaneously entrapped in LMCs. This is an especially desirable capability where such compounds produce complementary or synergistic effects. This multiplicity of entrapment may be achieved by placing the compounds in the organic or aqueous phase during LMC formation, depending upon their particular solubility properties.

The ultimate percentage of an agent that may be entrapped is dependent upon the physicochemical properties of the agent, the nature of the lipid components selected, the organic solvent and the manner in which the components are combined. Using the water-in-oil emulsion method, water soluble antibiotic incorporation of 30 to 70 percent has been observed, with a value of about 50 percent being typical. When water is eliminated as an ingredient, antibiotic incorporation of 90 to 100 percent has been observed. The degrees of entrapment for the lipid soluble compounds indomethacin and diazepam were 84 and 93 percent, respectively. (See Sections 6.2.1. and 6.2.2., infra.) As the initial concentration of material to be entrapped is increased, absolute LMC loading is increased at the expense of a relatively modest decrease in the percentage of entrapment [see Section 8, infra].

PHYSIOLOGICAL RESPONSES TO LMCs

Although LMCs may be administered subcutaneously, topically or by other routes, in the preferred mode of administration for release and distribution of the entrapped agent in vivo, LMCs are injected intramuscularly (IM). Placement in muscle tissue assures a controlled, slow release of entrapped materials and eliminates adverse physiological responses. The nature of the components of LMCs and their relatively brief duration of persistence in matrix form are such that there is no significant immunological reaction at the site of injection. Thus localized reddening of the surrounding tissue is not observed.

Although LMCs are preferably administered IM, their inadvertent escape into the vascular system would not create a risk of vascular occlusion. This is because LMCs are unstable in serum, readily degrading to form large oil droplets which, lacking rigidity, would not be hazardous. (See Section 9.1., infra.). In contrast to other carrier systems such as liposomes, the complete decay of LMCs allows for release of the entrapped compound at high levels during a period of time after which none of the compound remains in the system. In fact, the distributive pattern of LMC entrapped compounds in vivo is the same as would be expected with a free agent, but release from the depot is slow and sustained. This slow release permits the administration of larger effective doses of bioactive agents, without a corresponding increase in toxic effects.

In another embodiment, the LMCs of the present invention can be applied topically in order to obtain a localized sustained release of the entrapped agent. For example, topical application of LMCs to the skin results in retention and sustained release of the entrapped agent in the area of application. Thus, topical application may be particularly useful for the treatment of burns, wounds, and skin conditions such as acne. In such applications, the LMCs may contain antibiotics, vitamins, cell growth factors, etc. as the entrapped bioactive agent. Furthermore, LMCs may be used for oral, otic, ophthalmic, nasal, urethral, rectal, or vaginal administration of any appropriate bioactive agent.

EXAMPLE: PREPARATION OF LMCS

LMCs may be prepared by two basic methods, depending upon whether the compound to be entrapped is water or lipid soluble. These methods, with variations thereof, are detailed below. Egg phosphatidylcholine (EPC) was a product of Sigma Chemical Co., St. Louis, Missouri, while corn oil from Best Foods, CPC International Inc., Englewood, California was used as a source of triglycerides.

INCORPORATION OF WATER SOLUBLE MATERIALS

STREPTOMYCIN

In a preliminary step, acetone saturated with corn oil and EPC was prepared. This was carried out by adding 35 ml of corn oil dropwise with stirring to 40 ml of acetone at 4° C., until turbidity developed due to phase separation. Two additional ml of acetone were then added to restore a monophase, followed by the addition of EPC (approximately 240 mg) to the point of precipitation. Acetone (1.7 ml) was then added to form a final, clear solution.

Streptomycin (Sigma Chemical Co., St. Louis, Missouri) and $^{14}$C-sucrose (New England Nuclear, Boston, Massachusetts, 31.3 $\mu$Ci/m mole) were used together as model water soluble compounds for entrapment in conjunction with corn oil and EPC. The ratio of corn oil to EPC used to prepare the emulsion was 39:11 (weight/weight basis). The water-in-oil emulsion was prepared as follows: 6 ml of corn oil, 40 mg of EPC and 0.3 ml of phosphate buffered saline (PBS) containing 10 $\mu$l of $^{14}$C-sucrose and 100 mg of streptomycin were sonicated together for 45 seconds, using a Branson Model E sonicator at 22° C. The resulting water-in-oil emulsion was then extruded slowly through a 21 gauge syringe needle into 40 ml of the saturated acetone solution, with rapid stirring.

A cloudy suspension of LMCs resulted that was centrifuged at 10,000×g for 10 minutes at 4° C. The clear supernatant fluid was removed, and the pellet was washed three times with cold saturated acetone, dried under a nitrogen stream, and resuspended in 10 ml of PBS. The hydrated LMCs were then diluted with an equal volume of Ficoll-Paque (Pharmacia Fine Chemicals, Piscataway, New Jersey) and centrifuged at 10,000×g for 10 minutes. The LMCs, which floated to the top of the Ficoll-Paque gradient, were then isolated.

To determine the efficiency of entrapment, aliquots of the final LMC preparation were assayed by liquid scintillation counting. Results indicated that 96.5% of the initial amount of $^{14}$C-sucrose added to the preparation was entrapped in the LMCs.

The preparation of LMCs by the method described above proceeded by way of a water-in-oil emulsion which was injected into a saturated organic phase. Such an emulsion was avoided in a modification of the procedure wherein 0.3 ml of PBS containing 100 mg of streptomycin with 10 μl $^{14}$C-sucrose was added dropwise with stirring to 40 ml of the saturated acetone. The LMCs were isolated from the resulting suspension as described supra, and the final LMC product was comparable to the LMCs produced by way of emulsion.

GENTAMICIN

Lipid matrix carriers containing $^{125}$I-gentamicin (New England Nuclear, 100 mCi/m mole) were prepared using the water-in-oil method described in Section 6.1.1., except that the acetone was not saturated with corn oil and EPC. The LMCs thus produced contained 45 mg of gentamicin per 100 mg of LMC, with a specific activity of 0.2 μCi/100 mg gentamicin.

OXYTETRACYCLINE

LMCs containing oxytetracycline—HCl (Sigma Chemical Co., St. Louis, Missouri) were prepared by dissolving 100 mg of oxytetracycline-HCl in 0.4 ml of PBS, and vortexing the solution with 8 ml of corn oil containing 100 mg of EPC. The resulting water-in-oil emulsion was then slowly dropped through a 21-gauge syringe needle into 20 ml of an acetone solution in a Branson Model E bath sonicator. The acetone initially contained 100 mg of EPC and 2 ml of corn oil and was maintained at 8° C.

The LMCs that formed were then collected by centrifugation at 3,000×g for 5 minutes. Then, the precipitate was washed with more of the cold acetone solution, dried under nitrogen, resuspended in 10 ml of PBS, and subjected to Ficoll-Paque gradient centrifugation at 10,000×g for 10 minutes. The LMCs recovered from the top of the gradient entrapped 60% of the starting oxytetracycline-HCl determined by the following bioassay: 20 ml aliquots of the LMC preparation were plated onto S. aureus (ATCC 11632) lawns in nutrient agar (BBL Microbiological Systems, Becton Dickenson, Cockeysville, Maryland). The cultures were incubated for 24 hours at 37° C. The diameters of the resulting zones of inhibition were measured and compared to diameters obtained for known amounts of free drug.

INCORPORATION OF LIPID SOLUBLE MATERIALS

The procedure for forming LMCs with lipid soluble materials entrapped generally begins by dissolving the material to be incorporated in an appropriate organic solvent. Depending upon the solubility of the compound to be entrapped, chloroform, acetone or ethanol etc. might be preferable. Where it can be employed and where the ultimate use of the LMCs is to be IM or subcutaneous injection, ethanol is superior because of its less toxic character.

INDOMETHACIN

Ten mg of indomethacin (Sigma Chemical Co., St. Louis, Missouri) plus 10 μl of the $^{14}$C-labeled drug as a tracer (New England Nuclear, Boston, Massachusetts, 22 mCi/m mole) were dissolved in 1.5 ml of chloroform. This solution was then combined with 4 ml of corn oil and 150 mg of EPC, and the mixture was slowly extruded through a 21 gauge syringe needle into 20 ml of PBS at 45° C., with stirring. After combining all constituents, the mixture was roto-evaporated at 45° C. to remove the chloroform. One ml of the resulting suspension was then combined with an equal volume of Ficoll-Paque, the mixture was centrifuged at 10,000×g for 10 minutes, and the LMCs, which floated to the top of the gradient, were isolated.

Analysis of aliquots by liquid scintillation counting revealed that 84% of the starting amount of indomethacin had been incorporated into the LMCs.

DIAZEPAM

By following the procedure described in Section 6.2.1., supra, 5 mg of diazepam (Abbott Laboratories, N. Chicago, Illinois) with a trace of the $^3$H-labeled drug added (New England Nuclear, Boston, Massachusetts, 76.7 Ci/m mole) were incorporated into LMCs. The resulting diazepam-LMCs showed a 93% degree of entrapment.

EFFECT OF DRUG CONCENTRATION AND METHOD OF PREPARATION UPON LMC LOADING ACHIEVED

To determine the effect of initial drug concentration upon the level of final drug entrapment in LMCs, experiments were performed using increasing levels of bioactive agents, with the other components held constant for each method of preparation.

GENTAMICIN Six ml of corn oil, 40 mg of EPC, 0.3 ml of saline and 0.5 ml of saline containing either 25, 100 or 250 mg of gentamicin were sonicated together to form a water-in-oil emulsion which was then added with stirring to 40 ml of acetone and worked up as described in Section 6.1.2. To facilitate the analysis of the final LMC products, $^{125}$I-gentamicin had been added in tracer amounts to a final specific activity of 0.2 μCi/100 mg gentamicin. The isolated LMCs were then analyzed for gentamicin content by counting in a crystal gamma counter, and compared on a dry weight basis.

Table I surprizes these results.

TABLE I

ENTRAPMENT OF GENTAMICIN IN LMCs AS A FUNCTION OF INCREASING GENTAMICIN CONCENTRATION

| Gentamicin in Initial Preparation (mg) | Gentamicin in Product LMCs | |
|---|---|---|
| | % Entrapped | Total Entrapped (mg) |
| 25 | 60.4 | 15.2 |
| 100 | 52.9 | 52.9 |
| 250 | 47.2 | 118.0 |

As shown in Table I, increasing the antibiotic levels led to a decrease in the percentage of entrapment. Nevertheless, higher initial drug concentrations produced markedly higher final LMC concentration, a fact that should prove useful for therapeutic purposes.

OXYTETRACYCLINE

Varying amounts of oxytetracycline -HCl (Sigma Chemical, St. Louis, MO); i.e., 50 mg, 100 mg, 250 mg, 500 mg, 1 g, or 2 g, were added to a mixture of 8 ml palm oil (melted at 76° C.) and 100 mg EPC (N.B., no water was added to the mixture). Each mixture was extruded into 20 ml acetone (at 4° C.) previously saturated with 100 mg EPC and 100 mg oxytetracycline. The LMCs were precipitated and isolated as previously described and the amount of oxytetracycline present in the LMCs was analyzed by extracting the lipid components of 10 mg of each dry LMC preparation using a chloroform/hexane/water (2 ml/2 ml/1.8 ml) solvent system according to the method of Bligh and Dyer (1959, Can. J. Biochem. Physiol. 37:911) and measuring the absorbance of the aqueous phase and the organic phase of each extracted LMC preparation at a wavelength of 353 nm. Final concentrations of oxytetracycline on a weight basis were determined by comparisons to standard absorbance curves (at a wavelength of 353 nm) obtained for known concentrations of oxytetracycline in either organic or aqueous phases. The weight percent compositions and the efficiency of oxytetracycline entrapment in LMCs are presented in Table II.

TABLE II

DETERMINATION OF LMC COMPOSITIONS CONTAINING OXYTETRACYCLINE (OTC) BY EXTRACTION AND ABSORBANCE ANALYSIS

| OTC Added During Preparation (mg) | LMC Final Dry Weight (mg) | Lipids in LMC Product (mg) | Lipids in LMC Product % (Dry wt) | OTC in LMC Product (mg) | OTC in LMC Product % (Dry wt) | % Initial OTC Incorporated into LMCs |
|---|---|---|---|---|---|---|
| 200 | 460 | 306 | 66.5 | 154 | 33.5 | 77.0 |
| 350 | 810 | 459 | 56.7 | 351 | 43.3 | 100.0 |
| 600 | 1260 | 814 | 64.6 | 446 | 35.4 | 74.3 |
| 850 | 1550 | 823 | 53.3 | 726 | 46.7 | 85.4 |
| 1100 | 1870 | 775 | 41.4 | 1094 | 58.6 | 99.4 |
| 2100 | 2750 | 817 | 29.7 | 1932 | 70.3 | 92.0 |

The results in Table II demonstrate an extremely high efficiency of entrapment over a wide range of drug concentrations initially used in the preparation of LMCs. In addition, when high concentration of drug are used in the preparation of LMCs, the LMC incorporated lipid becomes constant whereas the concentration of entrapped drug increases (i.e., the ratio of incorporated drug to lipid increases).

EXAMPLE: USES OF LMCs

SUSTAINED RELEASE OF GENTAMICIN FROM LMCs AFTER INTRAMUSCULAR INJECTION IN MICE

To study the rate of release of a biologically active compound from LMCs, the behavior of LMC-entrapped and free gentamicin were compared in vivo.

Two groups of 25 g adult female Swiss Webster mice (Hilltop Farms, Scottsdale, Pennsylvania) were injected in a hind leg intramuscularly (IM) with 2.5 mg of gentamicin, either in free solution or entrapped in LMCs (prepared as described in Section 6.1.2), in 0.1 ml of physiological saline. At various periods following injection, one animal from each group was sacrificed, and the entire injected leg was removed and counted in a Beckman Gamma 5000 crystal gamma counter. The results may be seen in FIG. 1, in which closed circles represent free gentamicin, while open circles represent the LMC-entrapped drug.

Figure 1:
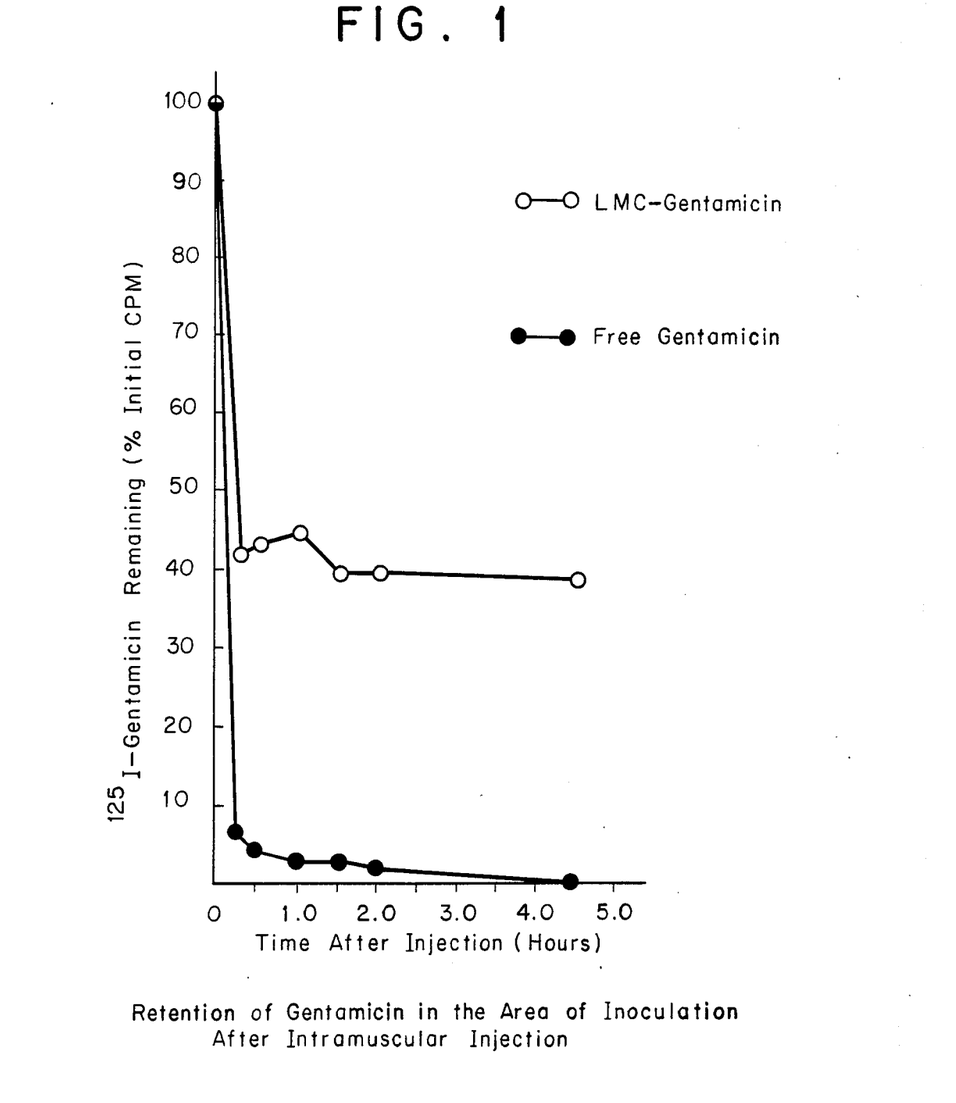
FIG. 1 is a graphical representation of the clearance of $^{125}$I-gentamicin from murine muscle tissues after intramuscular injection of LMCs containing the radiolabeled gentamicin and shows total radioactivity remaining as a function of time.

In both cases, there was an initial rapid decrease in the amount of gentamicin retained. For the free gentamicin, this decrease was complete by 4.5 hours post injection. For the LMC-entrapped gentamicin, tissue levels decreased slowly after an initial loss of approximately 60 percent. Even after 7 days (data not shown), about 12 percent of the initial gentamicin administered remained in the legs of the animals injected with the LMC preparation.

Figure 2:
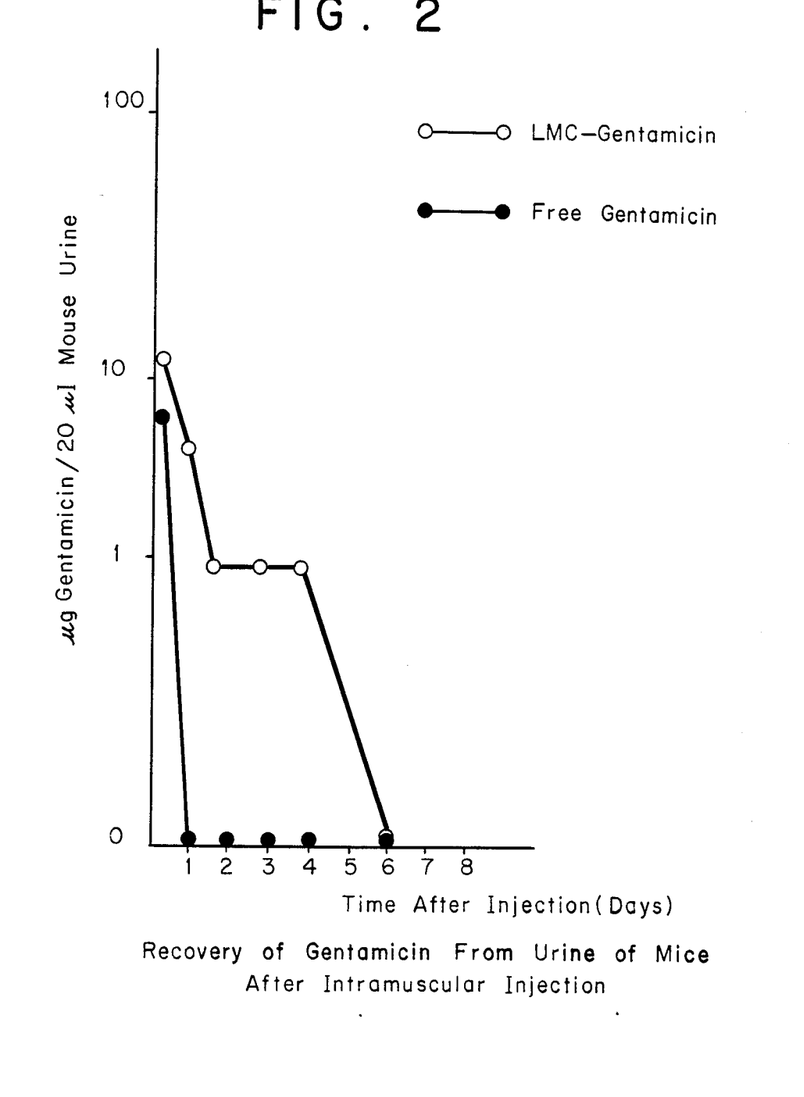
FIG. 2 is a graphical representation of the urinary excretion of $^{125}$I-gentamicin, from the experiment described in FIG. 1. Urinary gentamicin concentration is shown as a function of time.

In a parallel experiment, mice similarly injected with 2.5 mg unlabeled gentamicin were subjected to clean-catch urine analysis at various time intervals following injection. Twenty-μl aliquots from the urine samples collected were plated onto S. aureus (ATCC 11632) lawns in nutrient agar (BBL Microbiological Systems, Becton Dickenson, Cockeysville, Maryland). The cultures were then incubated for 24 hours at 37° C., when they were analyzed by measuring the diameters of the zones of bacterial growth inhibition. The concentrations of gentamicin in the urine samples were calculated by comparison to a standardized curve for the drug, and the results are shown in FIG. 2.

Urinary excretion of gentamicin in animals injected with the free drug (closed circles) reached zero by one day after injection. In contrast, animals injected with LMC-gentamicin (open circles) continued to excrete the drug until 144 hours after injection.

SUSTAINED RELEASE OF OXYTETRACYCLINE FROM LMCs AFTER INTRAMUSCULAR INJECTION IN MICE

LMCs containing oxytetracycline—HCl (Sigma Chemical Co., St. Louis, Missouri) were prepared as described in Section 6.1.3. supra. The LMCs thus produced contained 20 mg of oxytetracycline per ml of hydrated LMCs, as determined by the bioassay described in Section 6.1.3. Ten 25 g female adult Swiss Webster mice were then injected IM with 80 mg/kg of oxytetracycline in one hind leg, using either LMC-oxytetracycline or the free drug. In both cases, the antibiotic was administered in 0.1 ml of physiological saline.

Figure 3:
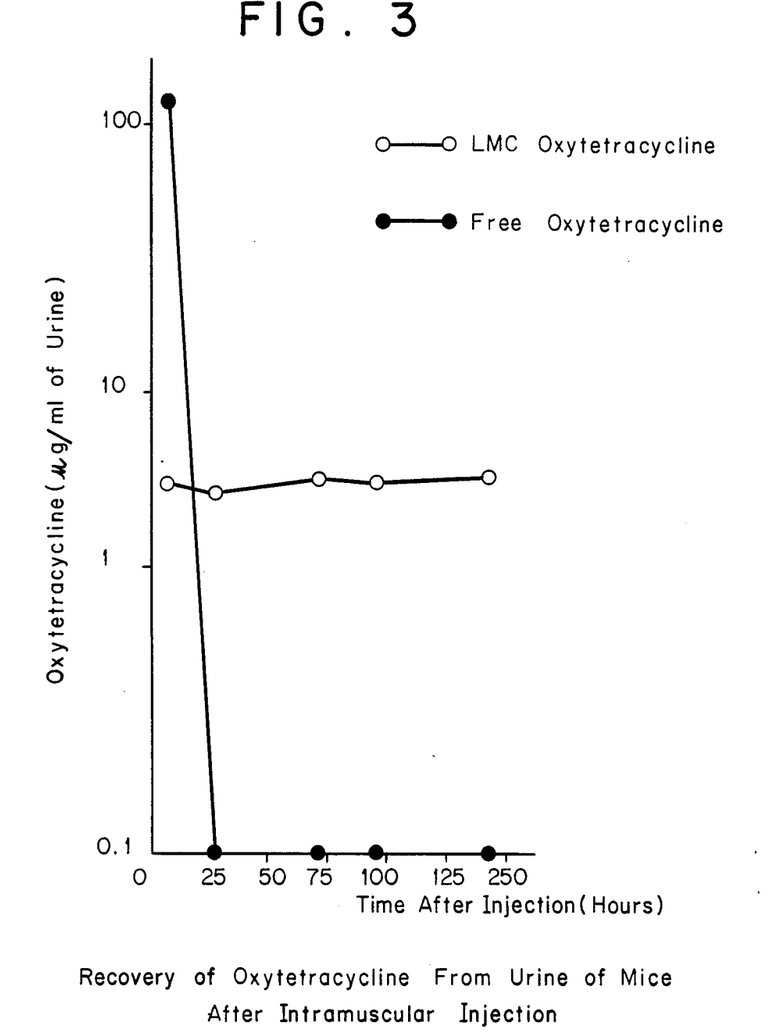
FIG. 3 is a graphical representation of the urinary excretion of oxytetracycline after IM injection in mice, with urinary concentrations of the antibiotic shown as a function of time.

At the times indicated in FIG. 3, samples of clean-catch urine were taken and aliquots were plated onto lawns of S. aureus (ATCC 11632) as described in Section 7.1. Antibiotic levels were quantified by comparison to an oxytetracycline standard curve. As shown in FIG. 3, the urinary levels of free oxytetracycline (closed circles) diminished to zero within 30 hours. In contrast, the slow release of the drug from LMCs caused a continuing and substantial level of release which persisted without diminution for 144 hours after injection. By 174 hours following injection, urinary levels of oxytetracycline were undetectable.

SUSTAINED RELEASE OF OXYTETRACYCLINE FROM LMCs AFTER SUBCUTANEOUS INJECTION IN MICE

LMCs containing oxytetracycline—HCl (Sigma Chemical Co., St. Louis, MO) were prepared as described in Section 6.3.2. supra, using either 100 mg, 250 mg, or 2 g oxytetracycline. The LMCs thus produced were suspended in saline. Each LMC preparation contained varying amounts of oxytetracycline per ml of hydrated LMCs. The final concentration of oxytetracycline in each preparation of LMCs was determined as described in Section 6.3.2.

Three groups of five 25 g female adult Swiss Webster mice were each injected subcutaneously with only one of the LMC preparations so that each mouse received 200 mg/kg oxytetracycline. In all cases, the LMC-drug preparation administered in 0.2 ml of physiological saline.

Figure 4:
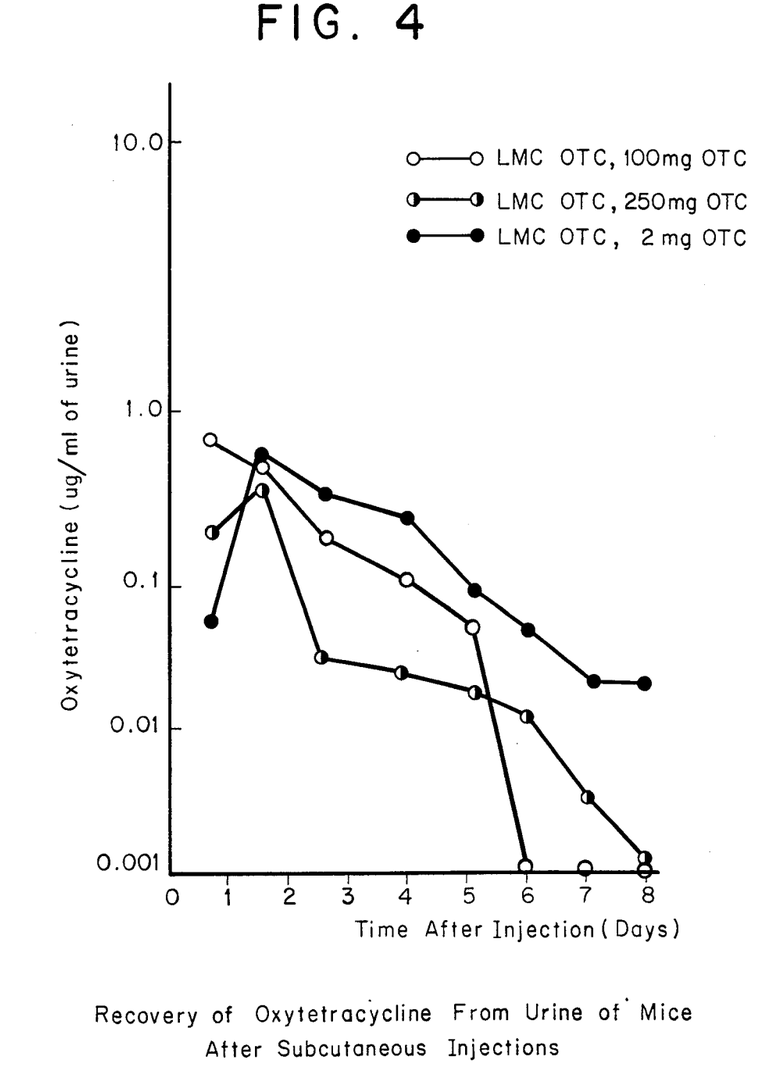
FIG. 4 is a graphical representation of the urinary excretion of oxytetracycline after subcutaneous injection in mice, with urinary concentrations of the antibiotic shown as a function of time.

Samples of clean-catch urine were taken daily and aliquots were plated onto lawns of S. aureus (ATCC 11632) as described in Section 7.1. Antibiotic levels were quantified by comparison to an oxytetracycline standard curve. As shown in FIG. 4, the slow release of drug from the LMCs resulted in a continuing and substantial urinary drug level, the persistance of which was proportional to the drug concentration of the LMC preparation administered; i.e., the higher drug: lipid ratio correlates with a more prolonged release.

EXAMPLE: STABILITY OF LMCs

LMCs IN SERUM

The LMCs of the present invention possess stability characteristics in serum that render them safe from the danger of vascular occlusion, when administered in vivo. Upon incubation in serum, LMCs break down to form larger structures that lack rigidity and resemble simple oil droplets. Because they are readily deformable, they could not cause vascular blockage. These stability characteristics are shown in FIG. 4.

In FIG. 4, the data are based upon the stability of streptomycin-LMCs in serum. LMCs were prepared as described in Section 6.1.1, using 6 ml of corn oil, 0.3 ml of PBS, 40 mg of EPC, 100 mg of streptomycin and 40 ml of acetone. Analysis showed that the LMCs thus produced contained 150 mg of streptomycin per ml of hydrated LMCs. One hundred mg of the streptomycin-LMCs were then incubated in 3.0 ml of non-heat-inactivated newborn calf serum at either 25° C. (closed circles) or 37° C. (open circles). At the times indicated, the absorbances of the samples at 400 and 600 nm were determined, and the 400/600 ratios were computed.

Sears (U.S. Pat. No. 4,298,594) has indicated that increases in plots of such absorbance ratios reflect an increase in particle size. Microscopic examination of aliquots of the LMC suspensions at various times confirmed the fact that coalescence into larger structures did occur. These structures were amorphous and readily deformable oil droplets that had lost the characteristics of LMCs. It thus seems likely that the potential for vascular occlusion present in some other lipid carriers does not exist in the LMCs of the present invention.

LMCs IN VIVO

To investigate the drug release characteristics of LMCs in vivo, gentamicin-LMC preparations were injected intraperitoneally (IP) into experimental animals. The final distribution of the drug was then compared with that of similarly injected free gentamicin.

LMCs were prepared as described in Section 6.1.2., using 6 ml of corn oil, 0.3 ml of PBS, 40 mg of EPC, 100 mg of gentamicin (with a small amount of I-gentamicin added as a tracer) and 40 ml of acetone. The resulting product contained 0.5 mg of gentamicin per mg of dry weight LMCs, as determined by gamma counting.

Two groups of 850 g female adult Hartley guinea pigs (Hilltop Farms, Scottsdale, Pennsylvania) were treated as follows: Animals in one group each received 0.3 ml of 100 µg/ml gentamicin in saline (with a small amount of $^{125}$I-gentamicin added as a tracer), IP. IP injection leads to rapid systemic distribution of the injected material. Animals in the other group received the same quantity of gentamicin entrapped in LMCs. At various times after injection pairs of animals were sacrificed, the hearts, spleens, kidneys and livers were removed, and the quantity of gentamicin in each organ was determined by counting in a crystal gamma counter. The results of these analyses are shown in Table III.

TABLE III

TISSUE DISTRIBUTION IN GUINEA PIGS OF GENTAMICIN INJECTED INTRAPERITONEALLY IN SALINE OR ENTRAPPED IN LMCs

| Organ | Gentamicin[1] Delivery Vehicle | Recovery of Gentamicin (% of Total Administered) Time After Administration (hours) | | | |
|---|---|---|---|---|---|
| | | 0.25 | 0.5 | 1.0 | 2.0 |
| Heart | Saline | 0.17 | 1.23 | 0.15 | 0.13 |
| | LMCs | 0.55 | 0.00 | 0.04 | 0.06 |
| Spleen | Saline | 0.09 | 0.08 | 0.05 | 0.04 |
| | LMCs | 0.00 | 0.06 | 0.00 | 0.00 |
| Kidney | Saline | 2.53 | 4.32 | 7.04 | 7.27 |
| | LMCs | 2.24 | 2.74 | 10.28 | 12.65 |
| Liver | Saline | 2.60 | 3.14 | 2.28 | 2.00 |
| | LMCs | 0.84 | 0.64 | 1.58 | 1.62 |

[1]Each animal received 0.3 ml of 100 mg/ml gentamicin sulfate.

As shown in Table III, the distribution of gentamicin to the tissues examined, whether the antibiotic was injected as the free form or entrapped in LMCs, was equally rapid. Thus the possibility that LMCs could persist in a stable large physical form that could produce vascular occlusion is extremely remote. Furthermore, the tissue distributions of ths two forms of gentamicin administered were also similar. It seems, therefore, that the release of entrapped materials from LMCs in free circulation following IP administration is very nearly equivalent to the administration of the free drug. The tissue distributions also show that the content of LMCs do not depot to an appreciable extent in liver or spleen, a problem that occurs with particulate microcarrier systems and that Gregoriadis (New England J. Med. 295:704(1976)) has found to occur with conventional liposomal microcarriers.

EXAMPLE: TREATMENT OF JOINT ARTHRITIS

Male white New Zealand rabbits (2–2.5 kg) were immunized intradermally, twice at two-week intervals, with 1 ml of 30 mg/ml bovine serum albumin (BSA) (Miles Laboratories, Elkhart, Indiana) emulsified in complete Freunds adjuvant. On the third week, the rabbits received a single intra-articular injection of 10 mg BSA in 1.0 ml of saline into the right knee joint to initiate joint arthritis. Left knee joints served as controls. The diameter of the joints was measured using a Fowler dial caliper, sensitive to 0.01 mm. The BSA-injected joints swell and typically measure 3–4 mm larger than uninjected control joints. On the fourth week, the rabbits received another intra-articular injection of BSA in saline to initiate inflammation in the same joint.

Indomethacin-LMCs were prepared as described in Section 6.2.1. Three days following the induction of the inflammation, BSA-injected animals received a single intramuscular injection of indomethacin-LMCs (1 mg indomethacin per animal). Joint swelling was measured for another ten days.

Figure 5:
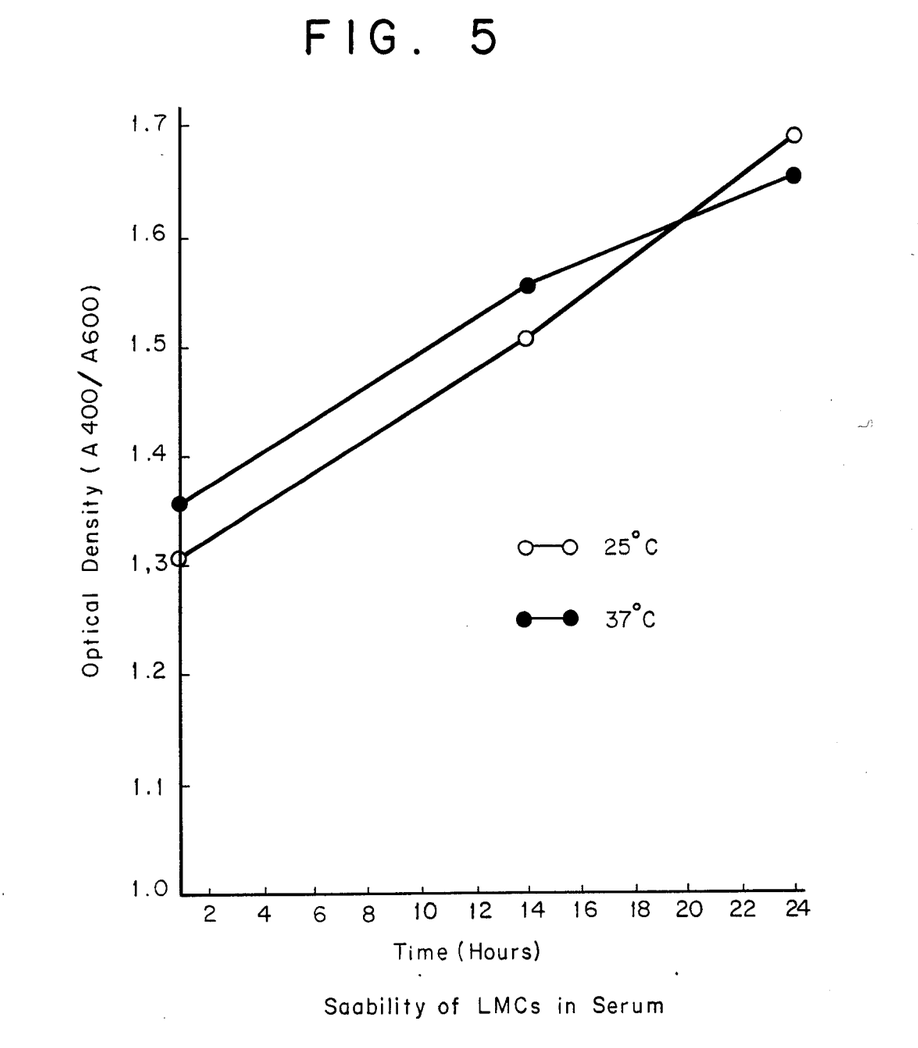
FIG. 5 is a graphical representation of the stability of LMCs in serum, showing changes in the 400/600 nm absorbance ratio (a measure of particle size) as a function of time.
Figure 6:
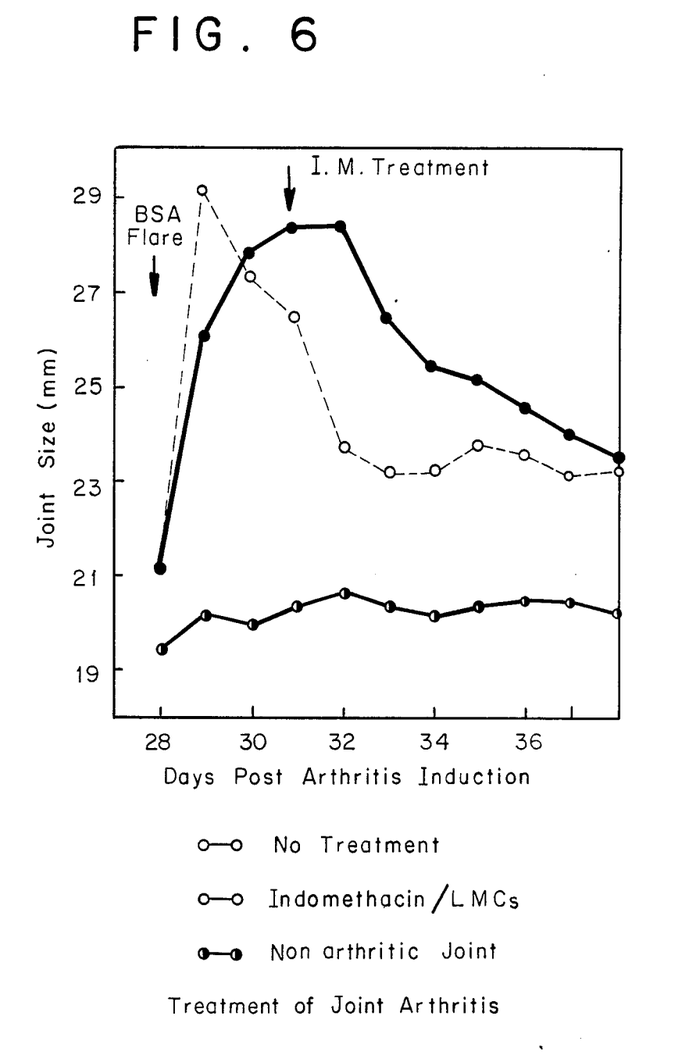
FIG. 6 is a graphical representation of the clinical effectiveness of indomethacin entrapped in LMCs when used to treat joint arthritis.

Results illustrated graphically in FIG. 5, indicate that the indomethacin-LMCs were effective in reducing joint swelling when administered intramuscularly.

EXAMPLE: TOPICAL ADMINISTRATION OF LMCs FOR LOCALIZED DELIVERY

In the following experiment, two groups of adult male Swiss Webster mice were treated with oxytetracycline as follows: 5 mice per group were depilitated on the back of their necks and 0.2 ml of 100 mg/ml oxytetracycline was topically applied to the depilitated area. The control group received oxytetracycline in PBS whereas the second group received oxytetracycline encapsulated in LMCs prepared as described in Section 6.1.3.

Clean catch urine samples were taken at 1, 18, 44, and 72 hours after topical application and aliquots were analyzed for the presence of oxytetracycline using the bioassay previously described in Sections 6.1.2, 7.1, and 7.2. No detectable levels of oxytetracycline were present in any of the samples, indicating that topical administration of the oxytetracycline-LMCs did not result in systemic release of the drug.

On a daily basis the treated area of each mouse was illuminated with ultraviolet light and inspected for fluorescence. Since oxytetracycline is fluorescent, the fluorescence of the treated skin is an indication of the presence of the drug in the skin. Fluorescence could be detected for only 2 days in the control group treated with the aqueous solution of oxytetracycline. Furthermore, the oxytetracycline could easily be washed off the control group using water. In contrast, fluorescence could be detected up to 4 days in the group that was treated with oxytetracycline-LMCs. In fact, the oxytetracycline could not be washed off with water and could only be removed by washing the skin with an organic solvent. These results indicate the penetration and enhanced retention of the drug in the area of skin to which the LMC-drug preparation was applied.

Many modifications and variations of this invention may be made without departing from its spirit and scope, as will become apparent to those skilled in the art. The specific embodiments described herein are offered by way of example only, and the invention is limited only by the terms of the appended claims.

What is claimed is:

1. Lipid matrix carriers comprising a hydrophobic compound, an amphipathic compound, and a bioactive agent combined in the form of globular structures having a diameter ranging from about 500 nm to about 100,000 nm, the amphipathic compound being present in an amount ranging from about 2% to about 50%, by weight, of the water insoluble components so that the globular structures are stabilized and so that upon administration in vivo the bioactive agent is released at a slow and sustained rate from the globular structures.

2. The lipid matrix carriers according to claim 1 in which the amphipathic compound is present in a range from about 2% to about 35%, by weight, of the water insoluble components of the globular structures.

3. The lipid matrix carriers according to claim 1 in which the amphipathic compound is present in a range from about 2% to about 25%, by weight, of the water insoluble components of the globular structures.

4. The lipid matrix carriers according to claim 1 in which the hydrophobic compound comprises a mixture of monoglycerides, diglycerides and triglycerides.

5. The lipid matrix carriers according to claim 1 in which the hydrophobic compound comprises a triglyceride or a mixture of triglycerides.

6. The lipid matrix carriers according to claim 4 in which the mixture of triglycerides comprises oils of fats.

7. The lipid matrix carriers according to claim 6 in which the mixture of triglycerides comprises vegetable oils.

8. The lipid matrix carriers according to claim 7 in which the vegetable oil comprises corn oil, palm kernal oil, coconut oil, soybean oil, sunflower oil, safflower oil, or cocoa butter.

9. The lipid matrix carriers according to claim 1 in which the hydrophobic compound comprises a sterol.

10. The lipid matrix carriers according to claim 11 in which the sterol comprises a cholesterol, a cholesterol ester, or derivatives thereof.

11. The lipid matrix carriers according to claim 1 in which the hydrophobic compound comprises a tocopherol or a derivative thereof.

12. The lipid matrix carriers according to claim 1 in which the hydrophobic compound comprises a petroleum jelly.

13. The lipid matrix carriers according to claim 1 in which the amphipathic compound comprises a surfactant.

14. The lipid matrix carriers according to claim 1 in which the amphipathic compound comprises an amphipathic lipid.

15. The lipid matrix carriers according to claim 14 in which the amphipathic lipid contains a hydrophilic phosphate group, carboxylic group, sulphato group, sulfhydryl group, amino group or nitro group.

16. The lipid matrix carriers according to claim 14 in which the amphipathic lipid contains a hydrophobic long chain aliphatic hydrocarbon group, aromatic group, cycloaliphatic group, or heterocyclic group.

17. The lipid matrix carriers according to claim 14 in which the amphipathic lipid is a phosphoglyceride.

18. The lipid matrix carriers according to claim 17 in which the phosphoglyceride is phosphatidylcholine, phosphatidylethanolamine, lysophosphatidylcholine, lysophosphatidylethanolamine, phosphatidylserine, phosphatidylinositol, phosphatidic acid, diphosphatidylglycerol, dimyristoylphosphatidylcholine, dipalmitoylphosphatidylcholine, distearoylphosphatidylcholine, dioleoylphosphatidylcholine, or dilinoleoylphosphatidylcholine.

19. The lipid matrix carriers according to claim 14 in which the amphipathic lipid is a sphingolipid, a glycosphingolipid, or derivatives thereof.

20. The lipid matrix carriers according to claim 14 further comprising a surfactant.

21. The lipid matrix carriers according to claim 1 in which the bioactive agent is water soluble.

22. The lipid matrix carriers according to claim 1 in which the bioactive agent is lipid soluble.

23. The lipid matrix carriers according to claim 1 in which the bioactive agent is selected from the group consisting of: antibacterial, antifungal, antiviral, and antiparasitic compounds.

24. The lipid matrix carriers according to claim 23 in which the entrapped bioactive agent comprises an aminoglycoside.

25. The lipid matrix carriers according to claim 24 in which the aminoglycoside is gentamicin or a derivative thereof.

26. The lipid matrix carriers according to claim 24 in which the aminoglycoside is streptomycin or a derivative thereof.

27. The lipid matrix carriers according to claim 23 in which the entrapped bioactive agent comprises a tetracycline.

28. The lipid matrix carriers according to claim 27 in which the tetracycline is oxytetracycline or a derivative thereof.

29. The lipid matrix carriers according to claim 23 in which the entrapped bioactive agent comprises a macrolide antibiotic.

30. The lipid matrix carriers according to claim 3 in which the macrolide antibiotic is tylosin or a derivative thereof.

31. The lipid matrix carriers according to claim 29 in which the macrolide antibiotic is erythromycin or a derivative thereof.

32. The lipid matrix carriers according to claim 1 in which the bioactive agent comprises a cell receptor binding compound.

33. The lipid matrix carriers according to claim 1 in which the bioactive agent is selected from the group consisting of: hormones, neurotransmitters, tumoricidal compounds, growth factors, and toxins.

34. The lipid matrix carriers according to claim 1 in which the bioactive agent is selected from the group consisting of: peptides, proteins, glycoproteins, and lipoproteins.

35. The lipid matrix carriers according to claim 34 in which the entrapped bioactive agent is an immunoglobulin.

36. The lipid matrix carriers according to claim 1 in which the bioactive agent comprises an immunomodulating compound.

37. The lipid matrix carriers according to claim 1 in which the bioactive agent is selected from the group consisting of catalysts and enzymes.

38. The lipid matrix carriers according to claim 1 in which the bioactive agent is selected from the group consisting: dyes, radiolabels, radio-opaque compounds and fluorescent compounds.

39. The lipid matrix carriers according to claim 1 in which the bioactive agent is selected from the group consisting of: anti-inflammatory, antiglaucomic, mydriatic, analgesic and anaesthetic compounds.

40. The lipid matrix carriers according to claim 39 in which the entrapped bioactive agent is indomethacin.

41. The lipid matrix carriers according to claim 1 in which the bioactive agent comprises a narcotic.

42. The lipid matrix carriers according to claim 41 in which the narcotic is diazepam.

43. The lipid matrix carriers according to claim 1 in which the bioactive agent is selected from the group consisting of: nucleic acids and polynucleotides.

44. The lipid matrix carriers according to claim 1 in which the bioactive agent is selected from the group consisting of: monosaccharides, disaccharides and polysaccharides.

45. The lipid matrix carriers according to claim 1 in which the bioactive agent comprises a vitamin.

46. A process for preparing lipid matrix carriers, comprising:
(a) emulsifying a mixture comprising an amphipathic compound combined with at least an equal amount by weight of a hydrophobic compound and a volume of aqueous phase ranging from about 0.7% to about 10.25% of the volume of the combined amphipathic compound and hydrophobic compound so that a water-in-oil emulsion is formed; and
(b) injecting the water-in-oil emulsion into a volume of organic solvent in excess of the volume of the water-in-oil emulsion, the organic solvent being capable of both solubilizing the amphipathic compound and removing water, so that lipid matrix carriers in the form of globular structures having a diameter ranging from about 500 nm to about 100,000 nm are formed, the amphipathic compound being present in an amount sufficient to stabilize the globular structures and the globular structures being further characterized as capable of releasing their contents in vivo or in vitro at a slow and sustained rate.

47. The process according to claim 46 further comprising removing the organic solvent.

48. A process for preparing lipid matrix carriers, comprising:
(a) combining an amphipathic compound with at least an equal amount by weight of a hydrophobic compound to form a mixture; and
(b) injecting the mixture into a volume of organic solvent in excess of the volume of the mixture, the organic solvent being capable of solubilizing the amphipathic compound, so that lipid matrix carriers in the form of globular structures having a diameter ranging from about 500 nm to about 100,000 nm are formed, the amphipathic compound being present in an amount sufficient to stabilize the globular structures and the globular structures being further characterized as capable of releasing their contents in vivo or in vitro at a slow and sustained rate.

49. The process according to claim 48 further comprising removing the organic solvent.

50. A process for the preparation of lipid matrix carriers, comprising:
(a) combining an amphipathic compound with at least an equal amount by weight of a hydrophobic compound in an organic solvent to form a solution; and
(b) adding the solution to an excess volume of aqueous phase with agitation so that lipid matrix carriers in the form of globular structures having a diameter ranging from about 500 nm to about 100,000 nm are formed, the amphipathic compound being present in an amount sufficient to stabilize the globular structures, and the globular structures being further characterized as capable of releasing their contents in vivo or in vitro at a slow and sustained rate.

51. The process according to claim 50 further comprising removing the organic solvent.

52. The process according to claim 46, 48 or 50 in which the hydrophobic compound comprises a mixture of monoglycerides, diglycerides, and triglycerides.

53. The process according to claim 46, 48 or 50 in which the hydrophobic compound comprises a triglyceride or a mixture of triglycerides.

54. The process according to claim 53 in which the mixture of triglycerides comprises corn oil.

55. The process according to claim 46, 48 or 50 in which the hydrophobic compound is a petroleum jelly.

56. The process according to claim 46, 48 or 50 in which the amphipathic compound comprises a surfactant.

57. The process according to claim 46, 48 or 50 in which the amphipathic compound comprises an amphipathic lipid.

58. The process according to claim 46, 48 or 50 in which the amphipathic lipid comprises a phospholipid.

59. The process according to claim 58 in which the phospholipid comprises phosphatidylcholine.

60. The process according to claim 46, 48 or 50 in which the amphipathic lipid is a sphingolipid or a derivative thereof.

61. The process according to claim 54 in which the amphipathic compound comprises 1 mg to 200 mg phosphatidylcholine which is combined with 6.2 g corn oil and in which the organic solvent is maintained at room temperature.

62. The process according to claim 54 in which the amphipathic compound comprises 1 mg to 200 mg phosphatidylcholine which is combined with 6.2 g corn oil and in which the organic solvent is maintained between 4° C. and 10° C.

63. The process according to claim 54 in which the amphipathic compound comprises 1 mg to 200 mg sphingomyelin which is combined with 6.2 g corn oil and in which the organic solvent is maintained at room temperature.

64. The process according to claim 54 in which the amphipathic compound comprises 1 mg to 200 mg sphingomyelin which is combined with 6.2 g corn oil and in which the organic solvent is maintained between 4° C. and 10° C.

65. The process according to claim 55 in which the amphipathic compound comprises 1 mg to 200 mg phosphatidylcholine which is combined with 6.2 g petroleum jelly and in which the organic solvent is maintained between 4° C. and 10° C.

66. The process according to claim 55 in which the amphipathic compound comprises 1 mg to 200 mg sphingomyelin which is combined with 6.2 g petroleum jelly and in which the organic solvent is maintained between 4° C. and 10° C.

67. The process according to claim 46, 48 or 50 further comprising the addition of a surfactant to the amphipathic compound.

68. The process according to claim 67 in which the surfactant comprises polyoxyethylene sorbitan monooleate.

69. The process according to claim 46 in which a water soluble bioactive agent is added to the aqueous phase.

70. The process according to claim 48 in which a bioactive agent is added to the mixture.

71. The process according to claim 50 in which a lipid soluble bioactive agent is added to the organic solvent.

72. The process according to claim 69, 70 or 71 in which the bioactive agent is selected from the group consisting of: antibacterial, antifungal, antiviral, and antiparasitic compounds.

73. The process according to claim 72 in which the bioactive agent comprises an aminoglycoside.

74. The process according to claim 73 in which the aminoglycoside comprises gentamicin or a derivative thereof.

75. The process according to claim 73 in which the aminoglycoside comprises streptomycin or a derivative thereof.

76. The process according to claim 72 in which the bioactive agent comprises a tetracylcine.

77. The process according to claim 76 in which the tetracycline comprises oxytetracycline or a derivative thereof.

78. The process according to claim 72 in which the bioactive agent comprises a macrolide antibiotic.

79. The process according to claim 78 in which the macrolide antibiotic comprises tylosin or a derivative thereof.

80. The process according to claim 78 in which the macrolide antibiotic comprises erythromycin or a derivative thereof.

81. The process according to claim 69, 70 or 71 in which the bioactive agent is a cell receptor binding compound.

82. The process according to claim 69, 70 or 71 in which the bioactive agent is selected from the group consisting of: hormones, neurotransmitters, tumoricidal compounds, growth factors, and toxins.

83. The process according to claim 69, 70 or 71 in which the bioactive agent is selected from the group consisting of: peptides, proteins, glycoproteins, and lipoproteins.

84. The process according to claim 83 in which the bioactive agent is an immunoglobulin.

85. The process according to claim 69, 70 or 71 in which the bioactive agent is an immunomodulating compound.

86. The process according to claim 69, 70 or 71 in which the bioactive agent is selected from the group consisting of catalysts and enzymes.

87. The process according to claim 69, 70 or 71 in which the bioactive agent is selected from the group consisting of: dyes, radiolabels, radio-opaque compounds, and fluorescent compounds.

88. The process according to claim 69, 70 or 71 in which the bioactive agent is selected from the group consisting of: anti-inflammatory, antiglaucomic, mydriatic, analgesic and anaesthetic compounds.

89. The process according to claim 88 in which the bioactive agent is indomethacin.

90. The process according to claim 69, 70 or 71 in which the bioactive agent comprises a narcotic.

91. The process according to claim 90 in which the narcotic comprises diazepam.

92. The process according to claim 69, 70 or 71 in which the bioactive agent is selected from the group consisting of: nucleic acids and polynucleotides.

93. The process according to claim 69, 70 or 71 in which the bioactive agent is selected from the group consisting of: monosaccharides, disaccharides, and polysaccharides.

94. The process according to claim 69, 70 or 71 in which the bioactive agent comprises a vitamin.

95. The process according to claim 46, 48 or 50 in which the organic solvent is acetone.

96. The process according to claim 95 in which the organic comprises 20 ml of acetone and the volume of the emulsion is 9 ml.

97. The process according to claim 46, 48 or 50 in which the organic solvent is chloroform.

98. The process according to claim 46, 48 or 50 in which the organic solvent is ethanol.

99. The process according to claim 46, 48 or 50 in which the organic solvent is diethyl ether.

100. The process according to claim 46, 48 or 50 in which the organic solvent is petroleum ether.

101. The process according to claim 46, 48 or 50 further comprising the step of separating the lipid matrix carriers from unincorporated components.

102. A method for the delivery in vivo of a bioactive compound comprising administering intramuscularly to a host the lipid matrix carriers of claim 1.

103. A method for the delivery in vivo of a bioactive compound comprising administering subcutaneously to a host the lipid matrix carriers of claim 1.

104. A method for the delivery in vivo of a bioactive compound comprising administering topically to a host the lipid matrix carriers of claim 1.

105. A method according to claim 104 in which the topical administration is oral, otic, ophthalmic, nasal, urethral, rectal or vaginal.

* * * * *